US007745136B1

(12) United States Patent
Dorsey

(10) Patent No.: US 7,745,136 B1
(45) Date of Patent: Jun. 29, 2010

(54) DIRECT QUANTIFICATION OF RIBOSOME INACTIVATING PROTEIN

(75) Inventor: Russell M. Dorsey, Joppa, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 12/362,599

(22) Filed: Jan. 30, 2009

(51) Int. Cl.
*C12Q 1/68* (2006.01)

(52) U.S. Cl. ......................... 435/6; 435/91.1; 435/91.2; 536/22.1; 536/23.1; 536/24.33

(58) Field of Classification Search ....................... None
See application file for complete search history.

*Primary Examiner*—Heather G. Calamita
(74) *Attorney, Agent, or Firm*—Ulysses John Biffoni

(57) ABSTRACT

A method for detecting ribosome inactivating protein (RIP) activity in a sample is provided that involves contacting a sample that contains an RIP with an inventive substrate that is depurinated to form product. The product is hybridized to a template and cleaved by an apurinic/apyrimidinic endonuclease such that releasing the blocked 3' end only in a sample that contains RIP activity. The 5' end of the product serves as a primer for extension by a polymerase reaction. The newly synthesized strand complementary to the template is detected by RT-PCR processes. A kit is provided suitable for field or laboratory use.

16 Claims, 7 Drawing Sheets

1. SYNTHETIC SUBSTRATE FOLLOWING EXPOSURE TO RIP RESULTING IN APURINIC SITE

5' CGACTGCTCAGACTACTCGATGGGGGGG-GACCCCCCC  BLOCKED (SEQ ID NO:2)
                                 5' GATCCCCCCCCTCGGGGCCGCGGTTGCGGATGTCTACACTCAGGCCATAGAATACGCTTCCATGTGAATTCGCGAATGACCTAGCCGATAGCCAATCTCGCAGT 5' C
                                 BLOCKED

2. CUT BY APE OR HEAT

-GACCCCCCC
5' CGACTGCTCAGACTACTCGATGGGGGGG
                              3'  GATCCCCCCCCTCGGGGCCGCGGTTGCGGATGTCTACACTCAGGCCATAGAATACGCTTCCATGTGAATTCGCGAATGACCTAGCCGATAGCCAATCTCGCAGT 5'
                              BLOCKED                                                                         (SEQ ID NO:5)

3. EXTEND WITH DNA POLYMERASE

5' CGACTGCTCAGACTACTCGATGGGGGGGGAGACCCCCGCGGCCCAACGCCTACAGATGGAGTCCGGTATCTTATGCGAAGGTACACTTAAGCGCTTACTGGATCGGCTATCGGTTAG
                                                                   3' GATCCCCCCCCTCGGGGCCGCGGTTGCGGATGTCTACACTCAGGCCATAGAATACGCTTCCATGTGAATTCGCGAATGACCTAGCCGATAGCCAATC 5'
                                                                                                                           (SEQ ID NO:5)

4. PCR AMPLIFICATION

5' CGACTGCTCAGACTACTCGATGGGGGGGGAGACCCCCGCGGCCCAACGCCTACAGATGGAGTCCGGTATCTTATGCGAAGGTACACTTAAGCGCTTACTGGATCGGCTATCGGTTAG 3'
                                                                                                      3' GACCTAGCCGATAGCCAATC 5'
                                                                                                                           (SEQ ID NO:3)

CGACTGCTCAGACTACTCGAT (SEQ ID NO:4)
3' GCTGACGAGTCTGATGAGCTAGATCCCCCCCCTCTGGGGGCCGCGGTTGCGGATGTCTACCCTCAGGCCATAGAATACGCTTCCATGTGAATTCGCGAATGACCTTAGCCGGATAGCCAATCTCGCAGT 5'

FIG. 10

SEQUENCE LISTING

```
<160> NUMBER OF SEQ ID NOS: 8

<210> SEQ ID NO 1
<211> LENGTH: 53
<212> TYPE: DNA
<213> ORGANISM: Artificial Sequence
<220> FEATURE:
<223> OTHER INFORMATION: completely synthesized
<220> FEATURE:
<221> NAME/KEY: miscellaneous feature
<222> LOCATION: (51)..(53)
<223> OTHER INFORMATION: dideoxy-cytosine

<400> SEQUENCE: 1
ggggttttgg gtttttttaa ttttaggttg tcggagacgt gttggttttt ccc          53

<210> SEQ ID NO 2
<211> LENGTH: 42
<212> TYPE: DNA
<213> ORGANISM: Artificial Sequence
```

```
<220> FEATURE:
<223> OTHER INFORMATION: completely synthesized
<220> FEATURE:
<221> NAME/KEY: miscellaneous feature
<222> LOCATION: (38)..(42)
<223> OTHER INFORMATION: dideoxy-cytosine

<400> SEQUENCE: 2
cgactgctca gactactcga tgggggggag accccccccc cc                           42

<210> SEQ ID NO 3
<211> LENGTH: 20
<212> TYPE: DNA
<213> ORGANISM: Artificial Sequence
<220> FEATURE:
<223> OTHER INFORMATION: right primer PCR detection of ribozyme
      inactivating protein

<400> SEQUENCE: 3
ctaaccgata gccgatccag                                                   20

<210> SEQ ID NO 4
<211> LENGTH: 21
<212> TYPE: DNA
<213> ORGANISM: Artificial Sequence
<220> FEATURE:
<223> OTHER INFORMATION: left primer PCR detection of ribozyme
      inactivating protein

<400> SEQUENCE: 4
cgactgctca gactactcga t                                                 21

<210> SEQ ID NO 5
<211> LENGTH: 108
<212> TYPE: DNA
<213> ORGANISM: Artificial Sequence
<220> FEATURE:
<223> OTHER INFORMATION: completely synthesized
<220> FEATURE:
<221> NAME/KEY: miscellaneous feature
<222> LOCATION: (106)..(108)
<223> OTHER INFORMATION: dideoxy-cytosine

<400> SEQUENCE: 5
tgacgctcta accgatagcc gatccagtaa gcgcttaagt gtaccttcgc ataagatacc       60
ggactcacat ctgtaggcgt tgcgccgggg gtctcccccc cctagccc                    108

<210> SEQ ID NO 6
<211> LENGTH: 119
<212> TYPE: DNA
<213> ORGANISM: Artificial Sequence
<220> FEATURE:
<223> OTHER INFORMATION: completely synthesized
<220> FEATURE:
<221> NAME/KEY: miscellaneous feature
<222> LOCATION: (117)..(119)
<223> OTHER INFORMATION: dideoxy-cytosine

<400> SEQUENCE: 6
tgacgctcta accgatagcc gatccagtaa gcgcttaagt gtaccttcgc ataagatacc       60
ggactcacat ctgtaggcgt tgcgaaaaac caacacgtct ccgacaacct aaaattccc       119

<210> SEQ ID NO 7
<211> LENGTH: 22
<212> TYPE: DNA
<213> ORGANISM: Artificial Sequence
<220> FEATURE:
```

-continued

```
<223> OTHER INFORMATION: nondegenerate probe for detection of ribozyme
      inactivating protein

<400> SEQUENCE: 7
cttaagtgta ccttcgcata ag                                              22

<210> SEQ ID NO 8
<211> LENGTH: 21
<212> TYPE: DNA
<213> ORGANISM: Artificial Sequence
<220> FEATURE:
<223> OTHER INFORMATION: forward primer PCR detection of ribozyme
      inactivating protein

<400> SEQUENCE: 8
ggggttttgg gtttttttaa t                                               21
```

DIRECT QUANTIFICATION OF RIBOSOME INACTIVATING PROTEIN

GOVERNMENT INTEREST

The invention described herein may be manufactured, used, and licensed by or for the United States Government.

FIELD OF THE INVENTION

The invention relates generally to a process of detecting enzymes in a fluid or solid sample; and in particular, to the detection of ribosome inactivating proteins in fluid media

BACKGROUND OF THE INVENTION

Ribosome inactivating proteins (RIPS, also known as ribotoxins) are toxic to animals and humans. RIPs exert their highly toxic action by catalytically inactivating ribosomes in eukaryotic cells that in turn inhibits protein synthesis leading to cellular destruction.

RIPs are generally divided into two classes, the Type I RIP and the Type II RIP. There is significant amino acid sequence homology between members of Type I and Type II RIPs, and bacterial Shiga and Shiga-like toxins. However, the Type II RIPs and the bacterial shiga and shiga-like toxins have similar mechanisms of action.

Abrin, ricin and shiga toxin belong to the type II RIP class. Type II RIPs are composed of two glycoproteins, an A-chain and a B-chain, which are joined by a disulfide bond. The B-chain mediates cellular internalization of the toxin via its high affinity for cell surface moieties and is capable of reversibly binding to a specific receptor on the cell membrane. Once bound to the specific receptor, the uptake of the A-chain into the cell is achieved through endocytosis. The A-chain then hydrolyzes the N-glycosidic bond on adenosine 4324 in the 28s subunit of eukaryotic ribosomal RNAs. This depurination subsequently prevents elongation factor 2 from binding to the ribosome resulting in loss of protein synthesis. For these reasons, Type 2 RIPs are very potent cytotoxins and animal poisons even at extremely low concentrations. The best known Type II RIP is ricin which has a median lethal dose ($LD_{50}$) of about 3 μg/kg.

Type I RIPs are typically composed of a single polypeptide chain that is equivalent in activity to the A-chain of Type II RIPs. Lacking analogs of the B-chain, Type I RIPs are minimally toxic to cells with intact membranes. However, in absence of cell membranes, Type I RIPs retain significant potency in inhibiting ribosomes and protein synthesis.

At the cellular level, Type II RIPs kill through the inhibition of protein synthesis in 1-3 hours. Depending on dose and route of exposure, clinical signs manifest between 8-24 hours. Of the many type II toxins known, abrin, ricin, and shiga toxin are classified as biological threat agents because of their wide availability and ease of production. Also, these type II RIPs are highly stable, amenable to dissemination, and are persistent in the environment once disseminated.

Type I and Type II RIPs may be derived from a variety of dicot and monocot plants, and thus can be found in many places. It has been theorized that they act as antiviral or antifungal agents. Type II RIPs possess the catalytically active A-chain, and retain depurination activity in ribosomes. Type II RIPs generally target a specific nucleotide sequence called the GAGA loop which is typically found in the large ribosomal RNA of eukaryotic cells, and enzymatically remove the first adenine base, (A), from the loop nucleotide sequence. For example, in rat liver cells, the A-chain removes a specific adenine base through cleavage of the glycosidic bond of adenine 4323 from 28S ribosomal RNA.

Type II MN including ricin have been studied and tested for use in weapon systems. Their extreme toxicity makes them potential candidates for use or deployment during warfare or acts of terrorism. In the event that Type II RIPs are ever deployed, part of the initial defense includes the rapid and accurate detection of RIPs, especially at submicrogram concentrations. Currently available military systems for detecting and identifying RIPs are laboratory based and require sophisticated and expensive equipment. Therefore, such systems are of limited practical use in the field.

Early detection in the laboratory and at any remote site of dissemination is essential for ensuring a prompt and appropriate response to a biological attack. The Department of Defense's (DoD's) field-forward identification process currently rely on molecular identification systems employing the Polymerase Chain Reaction (PCR) and immunological process to identify the presence of toxin in sample. The recent domestic attacks employing ricin via the postal system exposed several vulnerabilities of the current process that include their indirect identification of toxin and inability to directly quantitate the toxin's activity or distinguish between active and inactive toxin. These are significant limitations because ricin is easily produced through a number of processes that yield toxin with various purity and stability and thus lethality at the time of dissemination. Also, as techniques for generating genetic recombinants improve and become more widely available, the potential exists to develop a toxin that can defeat the indirect detection technologies.

It has recently been discovered that the Type II RIPs do not need the entire intact 28s ribosomal RNA to serve as a substrate, but a short strand of nucleotides containing a GAGA loop will suffice. Amukele T K and Schramm V L, *Biochemistry,* 2004; 43(17):4913-22. Current processes to assess the N-glycosidase activity of type II RIPs are arduous and lack sensitivity. For example, the direct fluorination 2-aminopurine analog method of U.S. Pat. No. 6,864,056 requires carefully handled substrates and large detection equipment. Moreover, direct labeling processes of the excised purine consistently suffer from low sensitivity, and are thus not amenable to use as a field detection technique for identification and assessment of RIP activity.

Accordingly, there is, a need to develop processes for rapidly detecting RIPs, particularly Type II RIPs, and related ribotoxins illustratively including ricin toxin A-chain (RTA), ricin, abrin, gelonin, SLT-1, and momordin that would permit protective measures or countermeasures to be quickly implemented in the event of an attack with weapons employing the same. There is also a need to provide an assay preferably in the form of a field kit that is sturdy, portable, rapidly deployable and simple to use. Moreover, the demand for processes and assays capable of rapidly detecting RIPs has applications beyond those of the military such as in the pharmaceutical, medical, food and public safety industries, and the like.

SUMMARY OF THE INVENTION

A process is provided for detecting activity of a ribosome inactivating protein wherein an oligonucleotide substrate containing a GAGA loop is reacted with a sample containing a ribosome inactivating protein to produce a product (an oligonucleotide substrate containing an abasic site). The product is hybridized to a second oligonucleotide, termed the template. Next, an endonuclease such as apurinic/apyrimidinic endonuclease is added which cleaves the substrate oligonucleotide at the abasic site. The hydrolysis by the endonuclease removes the block at the 3' of the substrate oligonucleotide. Removal of the 3' block allows for extension by a DNA polymerase to form an oligonucleotide strand complementary to said template that is thereby detected via PCR to discern the presence of ribosome inactivating protein in the sample.

Inventive substrates are provided that do not form stable stem-loop structures including those of sequences SEQ ID NO: 1 and SEQ ID NO: 2 which allow for substrate hybridization to the template.

Inventive templates are provided including those of sequences SEQ ID NO: 5 and SEQ ID NO: 6.

Identification of ribosome inactivating protein enzymatic activity is detected by illustratively real-time polymerase chain reaction (RT-PCR), mass spectrometry, or operative high pressure liquid chromatography (HPLC) for RT-PCR or for PCR detection primers of SEQ ID NO: 3 and SEQ ID NO: 4 are used.

Also, provided is a diagnostic assay process for detection of ribosome inactivating protein infection wherein a sample from a patient suspected of being infected with ribosome inactivating protein is contacted with a substrate and the enzymatic activity is detected.

A process for detecting ribosome inactivating protein in a sample is provided wherein an oligonucleotide substrate of SEQ ID NO: 1 is contacted with a sample containing a ribosome inactivating protein to produce a product that is hybridized to a template of SEQ ID NO: 6 and extended by a polymerization reaction to form an oligonucleotide strand complementary to the template which is detected by RT-PCR to identify the ribosome inactivating protein enzyme activity in the sample. A further step is provided wherein the substrate is cleaved by an endonuclease such as apurinic/apyrimidinic endonuclease prior to extension by the polymerization reaction. Processes are described for rapid and sensitive detection of ribosome inactivating proteins in human and animal biological samples as well as environmental samples and quantification thereof. Diagnostic kits are provided for detection of ribosome inactivating proteins in a clinical, laboratory, or field setting.

RT-PCR is used to detect the complementary strand using a probe of SEQ ID NO: 7 wherein the probe is hybridized under conditions suitable for a polymerase chain reaction; producing a first detection signal from said probe hybridized to the complementary strand. As such, the process diagnoses ribosome inactivating protein infection in a human. A second detection signal is optionally used that results from the hybridization of a probe complementary to a second template sequence. The second detection signal is generated in parallel with the first detection signal. The oligonucleotide strand complementary to the template is generated by PCR extension from a product generated by a purified and titered ribosome inactivating protein solution. Optionally, the first detection signal is compared to a third detection signal from a ribosome inactivating protein calibrator extracted in parallel to the sample. The calibrator comprises a known amount of ribosome inactivating protein and a known amount of a medium similar to the sample.

The detection signal is confirmed with a protein based ribosome inactivating protein detection assay such as an enzyme linked immunoadsorbent assay and a mass spectrometry assay.

A kit for detecting ribosome inactivating protein is provided that contains a substrate with sequence SEQ ID NO: 1; a template with sequence SEQ ID NO: 2; a reverse primer with sequence SEQ ID NO: 3; a forward primer with SEQ ID NO: 8; and a probe. The probe having the sequence of SEQ ID NO: 7.

BRIEF DESCRIPTION OF THE DRAWINGS

FIG. 10 is a process schematic of an overall detection of RIP activity by the inventive process using exemplary substrate, template, and primers.

DETAILED DESCRIPTION OF THE PREFERRED EMBODIMENTS

Figure 1:
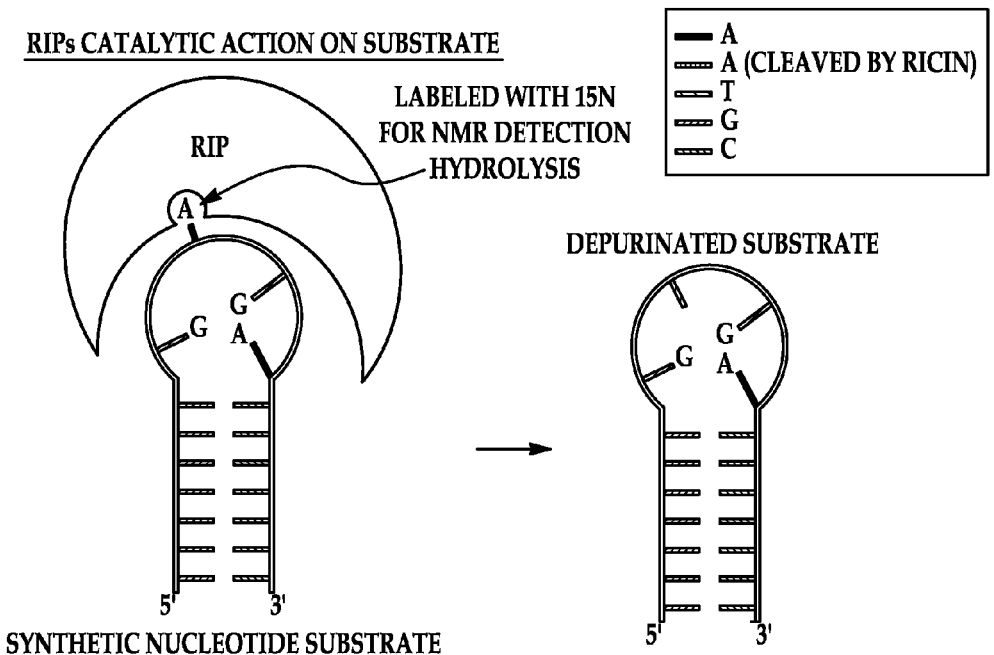
FIG. 1 is a schematic of an inventive substrate illustrating depurination of a nucleotide by a RIP.

The current invention has utility as a composition and assay for the sensitive and rapid detection of type I and II RIPs both in a laboratory and field setting. The technology also has the ability to detect any activity that results in cleavage of the an oligonucleotide.

The present invention is generally directed to a method, a reagent, and an assay kit useful for rapidly detecting the presence of RIPs, particularly Type II RIPs, and bacterial ribotoxins with similar mechanisms of action as those found in Type II RIPs, including, but not limited to, ricin toxin A-chain (RTA), momordin, ricin, abrin-A, gelonin, and SLT-1, in a sample suspected of containing the same. The method of the present invention is adapted for providing rapid and accurate detection of a range of Type II RIPs and Type II-like bacterial ribotoxins, and offering rapid deployability and easy implementation under various environmental conditions as required for military use, for example, under battlefield conditions.

The term "ribosome inactivating protein" or "ribotoxin" refers to any peptide, polypeptide, or other organic molecule produced naturally or synthetically which is capable of targeting and enzymatically releasing a specific base located within a specific base sequence in a nucleic acid substrate (i.e. first adenine base of the GAGA tetraloop) or cleaving the phosphate backbone of an oligonucleotide or DNA strand(s).

As used herein, the term "sample" is defined as sample obtained from a biological organism, a tissue, cell, cell culture medium, or any medium suitable for mimicking biological conditions, or from the environment. Non-limiting examples include, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, nasal secretions, water, air, gas, powder, soil, biological waste, feces, cell culture media, cytoplasm, cell releasate, cell lysate, buffers, or any other fluid or solid media.

The instant inventive processes are amenable to use for diagnosis of RIP infection in a patient. The term patient as used herein refers to a single or multicellular organism illustratively including, but not limited to, human, monkey, ape, upper and lower primates, horse, donkey, goat, rabbit, mouse, rat, guinea pig, hamster, mammals, non-mammals, insects, and any inclusive or other organism capable of infection or transfection by or with RIP.

The term "nucleotide" is intended to mean a base-sugar-phosphate combination either natural or synthetic, linear, circular and sequential arrays of nucleotides and nucleosides, e.g. cDNA, genomic DNA, mRNA, and RNA, oligonucleotides, oligonucleosides, and derivatives thereof. Included in this definition are modified nucleotides which include additions to the sugar-phosphate groups as well as to the bases.

The term "nucleic acid" refers to multiple nucleotides attached in the form of a single or double stranded polynucleotide that can be natural, or derived synthetically, enzymatically, and by cloning processes. The term "oligonucleotide" refers to a polynucleotide of less than 200 nucleotides. The terms "nucleic acid" and "oligonucleotide" may be used interchangeably in this application The minimal size of an oligonucleotide substrate is of a size sufficient to form a stable hybrid with the complementary sequence of a nucleic acid molecule template for the APE action and PCR. Specific requirements for the substrate oligonucleotides is that it contains a GAGA sequence, a block to DNA polymerase at the 3' end (dideoxy C) and a region complementary to the template oligonucleotide to allow for hybridization of the substrate and template. The template must also contain a block to DNA polymerase and region complementary to the substrate oligonucleotide.

A method for the rapid and sensitive detection of RIPs in a sample is provided. In a preferred embodiment, a sample is provided that is contacted with a substrate oligonucleotide containing a GAGA loop. Should a RIP be present in the sample, the first adenosine base of the GAGA sequence is removed from the substrate producing an oligonucleotide with a abasic site. The sample including product is contacted with a template oligonucleotide strand that is complementary in part to the substrate oligonucleotide and the two strands are hybridized. The abasic substrate is cleaved illustratively by an APE, and the remaining 5' end acts as a primer for extension and synthesis of strand complementary to the template strand. The extended primer is then detected via real-time PCR.

A sample is preferably a fluidic sample. Illustratively, a fluidic sample such as serum or cell lysate is diluted in a buffered saline solution suitable for activity of a therein contained RIP. Alternatively, a sample is solid wherein a suspension is created in a buffered saline solution or the solid is dissolved in a solvent such as a buffered saline solution. An illustrative example of operative buffered solutions are 50 mM Tris-HCl, 10 mM MgCl$_2$, 100 mM NaCl, pH 8.0 or 25 mM Tris/HCl, pH 7.6, 25 mM KCl, 5 mM MgCl$_2$. It is appreciated that other buffered or non-buffered solutions are similarly operable. Other buffers operable are illustratively, HEPES, Tris, phosphate, carbonate, imidizole, acetate, or any other buffer known in the art. Salts and other cations are further operable in the subject invention. (See e.g. Endo, Y, et al, *J Biol Chem*, 1987; 262:8128-30.) Preferably, magnesium ions are included in a buffer or solution. Endo, Y, *J Biol Chem*, 1988; 263:8735-8739. More preferably, magnesium is between 5 and 15 mM.

A substrate is illustratively any molecule or composition capable of being modified by a RIP. Preferably, a substrate is an oligonucleotide with a GAGA loop. More preferably, a substrate has a stem-loop secondary structure encompassing a GAGA loop. Most preferably, a substrate is an oligonucleotide of the sequence in SEQ ID NO: 1. Alternatively, a substrate is of the sequence SEQ ID NO: 2. In a preferred embodiment the stem-loop structure is thermodynamically unstable. The length of the hairpin structure is preferably less than 20 nucleotides. More preferably, the length of the hairpin structure is less than 10 nucleotides. Most preferably, the length of the hairpin structure is 8 nucleotides or less. The length and sequence of the hairpin structure is preferably such that it will not produce false amplification positives in the absence of exposure to a RIP. Surprisingly, while a stable stem loop or a stem loop of greater length than that of SEQ ID NO: 1 is expected to be a more efficient substrate for a RIP, a thermodynamically unstable stem-loop structure surprisingly produces a lower false positive rate, thus, enhancing the specificity and detectability of a RIP in the invention. As such, a length of stem-loop that is thermodynamically unstable is preferred. Most preferably, substrate dA-8 (SEQ ID NO: 1) is used.

Contacting a sample containing RIP with an inventive substrate results in modification of the substrate. Illustratively, all Type I and Type II RIPs possess RNA N-glycosidase activity. (see Peumans, W J et al., *FASEB J*, 2001; 15:1493-1506.) Ricin, abrin, and Shiga toxin illustratively depurinate an inventive substrate at an adenine in a GAGA loop. Trichosanthin also possess phosphatase activity that will cleave a substrate such that subsequent cleavage by APE may not be absolutely necessary in the inventive process, depending on the sample concentration of the RIP(s). (FIG. 1.)

As all type I and type II RIPs possess depurination activity on RNA and DNA (see Barbieri, L, et al, *Biochem. J*, 1996; 319, 507-13), the inventive method preferably detects depurination activity of a RIP in a sample.

An inventive substrate preferably has a cap or a block at the 3' end so that it will not act as a primer for extension by a polymerase. A cap is illustratively one or more spacers or depurinated nucleotide(s). Other caps and capping mechanisms known in the art are similarly operable and illustratively include a phosphate cap, fluorescent dye, an alkyl group such as a C3-carbon spacer, biotin, FAM, 6-HEX, combinations thereof, or other modifications at the 3' end or suitably close thereto. Illustratively, an internal modification operable to block the substrate 3' end from acting as a primer for a polymerization reaction is operable herein.

Figure 2:
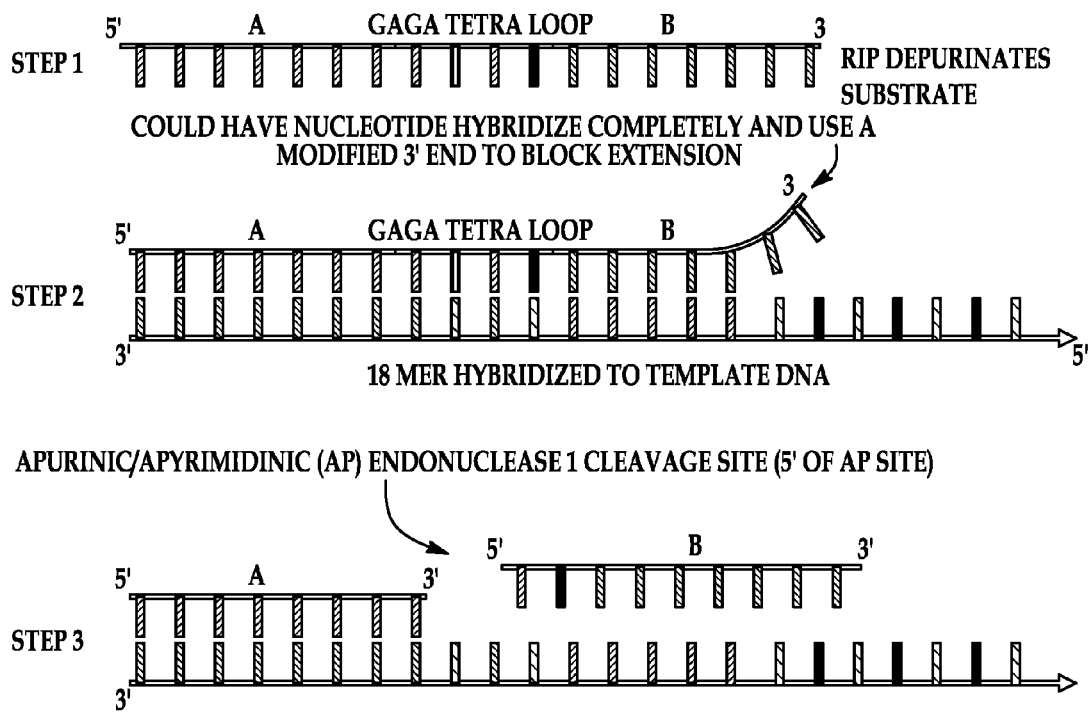
FIG. 2 is a schematic of a hybridization to template DNA and APE. The depurinated substrate is hybridized to a synthetic DNA template for APE cleavage of the phosphodiester backbone. The resulting fragment (labeled A) serves as a primer for subsequent PCR amplification and detection. The 3' fragment of the depurinated substrate is a detectable fragment (labeled B) under hybridization conditions for A with the template.

An inventive substrate preferably has an A sequence and a B sequence. (FIG. 2.) The A sequence is illustratively the region 5' to the depurination site. The B chain is illustratively the region 3' to the depurination site. In a preferred embodiment the melting temperature (Tm) of the A sequence is higher than that of the B sequence. Following cleavage of the product (depurinated substrate) by a nuclease, increasing the temperature of the product/template hybridized molecule will melt the association of the B sequence prior to melting of the A sequence region. In a preferred embodiment the Tm of the B sequence is low enough that during a subsequent detection step the temperature of the reaction never reaches a temperature that will allow hybridization of the B sequence with the template. Alternatively, a DNA polymerase can be employed that is hydrolyze the B sequence thus removing it from the reaction mixture.

Contacting the sample containing a RIP with an inventive substrate produces a product that is preferably a depurinated substrate at an adenine in the GAGA loop due to the N-glycosidase activity of the RIP. (FIG. 1.) A template molecule is provided. The template molecule preferably has a sequence complementary to a region of the substrate. (FIG. 2.) It is appreciated that any length of hybridization region is operable herein. Preferably, the template molecule is a sequence with excellent and specific hybridization properties with at least the A chain of the product. In a preferred embodiment the product overhangs the template at the 3' end of the template. It is appreciated that a blunt end is similarly operable from the 5' end of the product and the 3' end of the template hybridizing at the same base pair. It is further appreciated that the 3' end of the template may operably extend beyond the 5' end of the product.

The template is optionally capped at the 3' end such that a polymerization reaction cannot take place from this end of the molecule. A cap is illustratively one or more spacers or depurinated nucleotide(s). Other caps and capping mechanisms known in the art are similarly operable and illustratively include a phosphate cap, fluorescent dye; an alkyl group such as a C3-carbon spacer, biotin, FAM, 6-HEX, combinations thereof, or other modifications at the 3' end or suitably close thereto. Illustratively, an internal modification operable to block the template 3' end from acting as a primer for a polymerization reaction is operable herein.

In a preferred embodiment a template is between 25 and 200 residues or nucleotides long. More preferably a template is between 50 and 150 nucleotides long. Most preferably, an inventive template is between 80 and 120 nucleotides long.

A template molecule has a sequence such that there is only one hybridization site for the product. It is appreciated that a template with more than one hybridization site is operable herein. Preferably, the hybridization site for association with the product is at or near the 3' end of the template.

Upon hybridization of the product with the template reaction conditions are altered such that cleavage of the substrate at the depurinated site is achieved. (FIG. 2.) It is appreciated that cleavage of the substrate is optionally cleaved prior to hybridization with the template. Cleavage is preferably performed by an apurinic/apyrimidinic endonuclease (APE). Any APE known in the art is operable herein. Preferably an APE is human AP-endonuclease. Zaky, A, et al., *Nucleic Acids Res*, 2008; 36: 1555-1566. It is appreciated that an APE is natural, synthetic, recombinant, a mutation of a known sequence, or otherwise. It is appreciated that an APE is illustratively an endonuclease from a mammal or other organism. Illustratively, an APE operable herein includes APE1, Apn1, Apn2, and other APEs known in the art, mutations thereof, or combinations thereof. It is further appreciated that an APE may function downstream from another break modifier such as Ntg1 and Ntg2, or other enzyme or chemical modifier known in the art. Preferably, an APE is heat stable. APE1 may be obtained from New England Biolabs, Ipswich, Mass.

Other processes of cleaving the product at the AP site illustratively include, heat, β-elimination, KWK tripeptide cleavage, or other mechanisms known in the art. Conditions and reagents for these reactions are known in the art.

In the inventive method, cleavage of the AP site separates the A chain and the B chain. (FIG. 2, step 3; FIG. 10.) Either by an unstable hybridization of the B chain with the template or by heat and melting, or by using a DNA polymerase with 5' to 3' exonuclease activity. The 5' end of the A chain in the product is unblocked following the cleavage reaction by the APE. Thus, the A chain may act as a primer for polymerase activity in a polymerization reaction.

Figure 3:
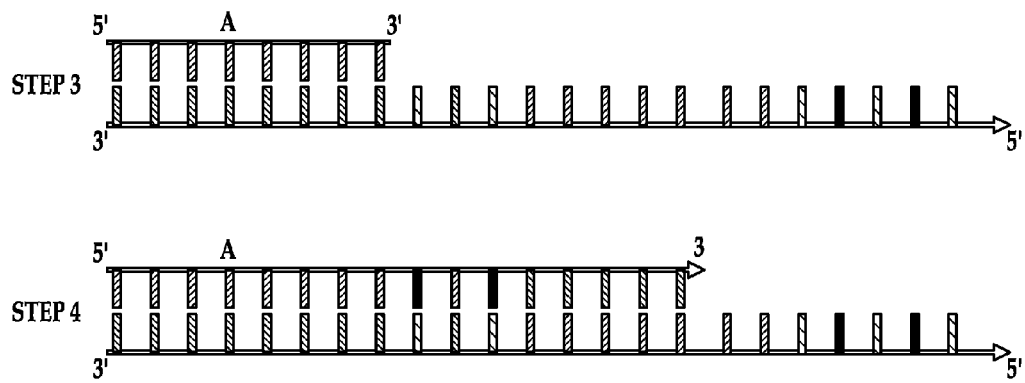
FIG. 3 is a schematic of the remaining A chain following endonuclease cleavage of FIG. 2 used as a primer for a subsequent polymerization reaction such as PCR.
Figure 4:
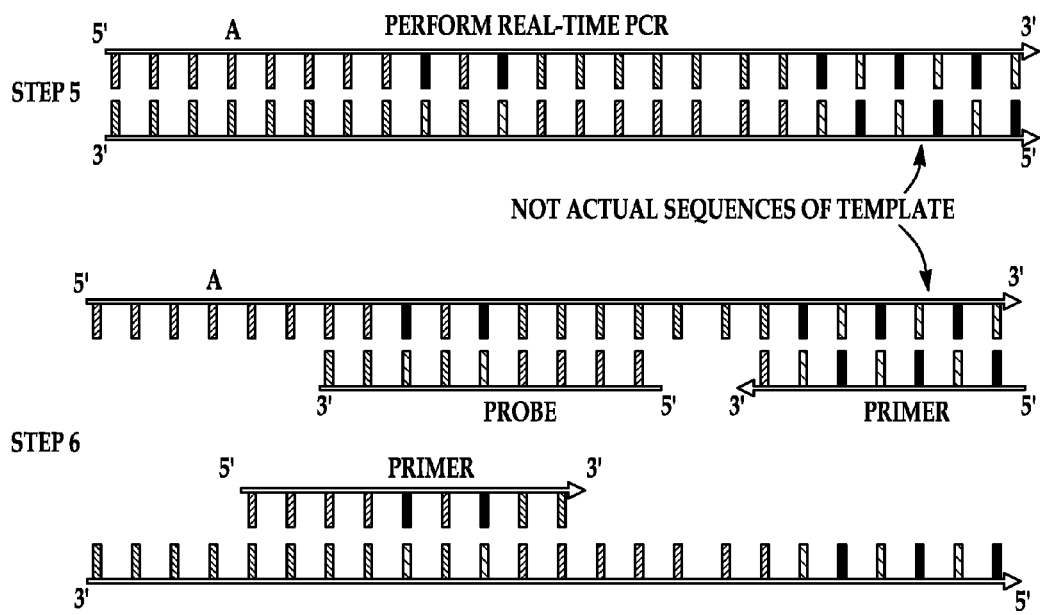
FIG. 4 is a schematic of represents, a RT-PCR subsequent to the sequence of FIG. 3 reaction for detection of a RIP dependent complementary oligonucleotide strand.
Figure 5:
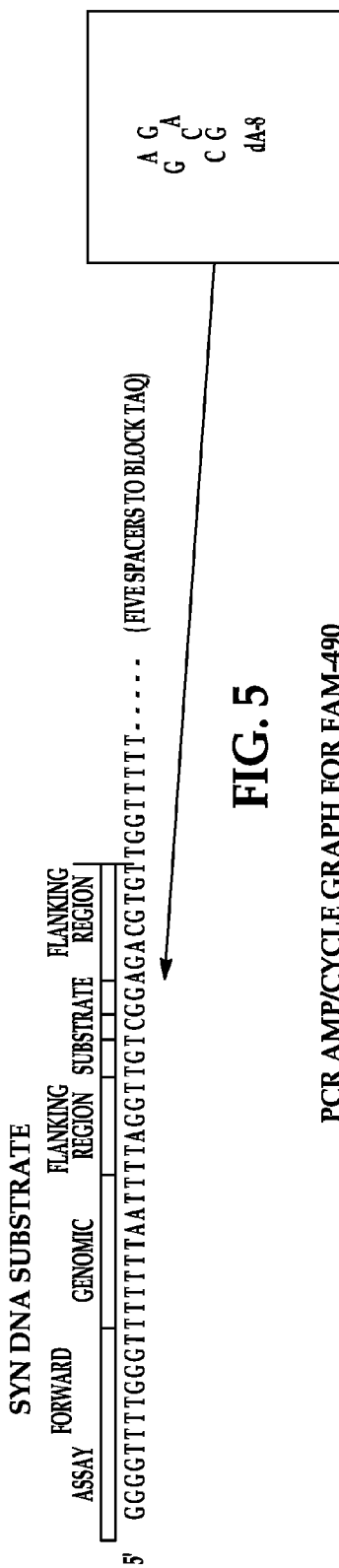
FIG. 5 is a schematic of a preferred substrate, the dA8 substrate that does not form a stable stem-loop.

The inventive method further comprises a polymerization reaction. (FIGS. 3 and 10.) The polymerization reaction is performed by a nucleic acid polymerizing enzyme that is illustratively a DNA polymerase, RNA polymerase, reverse transcriptase, mixtures thereof, or other polymerases known in the art. It is further appreciated that accessory proteins or molecules are present to form the replication machinery. In a preferred embodiment the polymerizing enzyme is a thermostable polymerase or thermodegradable polymerase. Use of thermostable polymerases is well known in the art such as Taq polymerase available from Invitrogen Corporation, Carlsbad, Calif. Thermostable polymerases allow a polymerization reaction to be initiated or shut down by a change in temperature or other condition in the sample without destroying activity of the polymerase.

It is further appreciated that the proteinaceous material of the polymerization enzyme in the case of a DNA polymerase is optionally immobilized on a solid support surface either reversibly or irreversibly. For example, RNA polymerase was successfully immobilized on an activated surface without loss of catalytic activity. Yin et al., *Science*, 1995; 270: 1653-57. Alternatively, an antibody antigen pair is utilized to bind a polymerase enzyme to a support surface whereby the support surface is coated with an antibody that recognizes an epitope on the protein antigen. When the antigen is introduced into the reaction chamber it is reversibly bound to the antibody and immobilized on the support surface. A lack of interference with catalytic activity in such a method has been reported for HIV reverse transcriptase. Lennerstrand, *Analytical Biochemistry*, 1996; 235:141-152. Additionally, DNA polymerase immobilization has been reported as a functional immobilization method in Korlach et al., U.S. Pat. No. 7,033, 764 B2. Finally, any protein component can be biotinylated such that a biotin streptavidin interaction is optionally created between the support surface and the target immobilized antigen.

Accuracy of the base pairing in the preferred embodiment of a polymerization reaction is provided by the specificity and fidelity of the polymerization enzyme. Error rates for Taq polymerase tend to be false base incorporation of $10^{-5}$ or less. Johnson, *Annual Reviews of Biochemistry*, 1993: 62:685-713; Kunkel, *Journal of Biological Chemistry*, 1992; 267:18251-18254. Specific examples of thermostable polymerases illustratively include those isolated from *Thermus aquaticus, Thermus thermophilus, Pyrococcus woesei, Pyrococcus furiosus, Thermococcus litoralis* and *Thermotoga maritima*. Thermodegradable polymerases illustratively include *E. coli* DNA polymerase, the Klenow fragment of *E. coli* DNA polymerase, T4 DNA polymerase, T7 DNA polymerase and other examples known in the art. It is recognized in the art that other polymerizing enzymes are similarly suitable illustratively including *E. coli*, T7, T3, SP6 RNA polymerases and AMV, M-MLV, and HIV reverse transcriptases.

The inventive method provides a rapid, specific, and sensitive assay method for detection of RIPs in biological samples comprising creating a depurination specific primer (product) by specific RIP activity hybridized to an oligonucleotide template. The A sequence product of an APE reaction cleaving the A and B sequences serves as a primer for synthesis of a complementary strand to an oligonucleotide template. (FIGS. 3 and 10.) In subsequent reactions an oligonucleotide reverse primer with a nucleotide sequence complementary to a unique sequence in the newly RIP dependent extended complementary strand oligonucleotide is hybridized to its complementary sequence and extended. (FIGS. 3 and 10.) Similarly, a forward oligonucleotide primer representative of a region in the 3' end of the A chain and preferably beyond the capped 3' end of the template is hybridized and extended. This system allows amplification of specific oligonucleotide sequences dependent on an initial extension of an A chain primer resulting from RIP activity and is suitable for simultaneous or sequential detection systems.

In a preferred embodiment, a real-time PCR (RT-PCR) assay system is employed such as the TAQMAN system available from Applied Biosystems (Foster City, Calif.) or the iCycler iQ real-time detection system (Bio-Rad, Hercules, Calif.). (FIGS. 3 and 10.) It is appreciated that a probe based method, intercalator-based method, or other method known in the art is operable herein. Oligonucleotide probes are selected based on unique regions of the template oligonucleotide. Illustrative examples of probes, primers, template, and substrate are provided in FIG. 10. In this embodiment the detection signal is illustratively achieved by probe binding the newly synthesized RIP specific complementary strand oligonucleotide. Suitable probes are optionally between 15 and 30 nucleotides long, are unique to the target sequence, are not prone to dimerization, and do not possess repeat regions. Processes of probe design and considerations for use are recognized in the art.

Preferably, probes possess nucleotide sequences complementary to either the template DNA or the RIP dependent complementary strand. A primer is optionally complementary to a region overlapping the A chain and B chain of the product so that detection is restricted to extended A chain due to RIP activity. More preferably, primers contain the nucleotide sequences of SEQ ID NOs: 3 or 4. It is appreciated that the complement of SEQ ID NOs: 3 and 4 are similarly operable for use in the instant invention. It is further appreciated that oligonucleotide sequences that hybridize with SEQ ID NOs: 3 or 4 are also similarly operable. Finally, multiple positions are optionally available for hybridization on the template and complementary strands.

Any suitable fluorescent probe for use in RT-PCR detection systems is illustratively operable in the instant invention. Similarly, any quenching molecule for use in RT-PCR systems is illustratively operable. In a non-limiting example any of the AlexaFluor dyes such as AlexaFluor 495 or 590, Cascade Blue, Marina Blue, Pacific Blue, Oregon Green, Rhodamine, Fluoroscein, TET, HEX, Cy5, Cy3, Tetramethylrhodamine, or other suitable fluorescent dyes are operable herein. Quenching molecules are suitably matched to the fluorescence maximum of the dye. It is appreciated that other detection systems, techniques, and labels are operative herein. Illustratively, a probe is labeled with a radioactive marker. Illustrative radioactive labels include $^3H$, $^{13}C$, $^{32}P$, $^{125}I$, $^{131}I$, $^{22}Na$, $^{51}Cr$, and other radioactive labels known in the art.

In a further embodiment detection of PCR products is achieved by mass spectrometry. Mass spectrometers are prevalent in the clinical laboratory. Similar to fluorescence based detection systems, mass spectrometry is capable of simultaneously detecting multiple amplification products for a multiplexed and controlled approach to accurately quantify components of biological or environmental samples.

Multiple mass spectrometry platforms are suitable for use in the instant invention illustratively including matrix assisted laser desorbtion ionization time of flight mass spectrometry (MALDI), electrospray mass spectrometry, electrospray ionization-Fourier transform ion cyclotron resonance mass spectrometry (ESI-FTICR), multi-stage mass spectrometry fragmentation analysis (MS/MS), mass spectrometry coupled with liquid chromatography such as high performance liquid chromatography mass spectrometry (HPLC) and ultra performance liquid chromatography isotope dilution tandem mass spectrometry (HPLC-ID/MS/MS), and variations thereof.

It is appreciated that numerous other detection processes are similarly suitable for measuring an amplification product by detecting a detection signal. Illustrative examples include, but are not limited to, liquid chromatography, mass spectrometry, liquid chromatography/mass spectrometry, static fluorescence, dynamic fluorescence, high performance liquid chromatography, ultra-high performance liquid chromatography, enzyme-linked immunoadsorbent assay, real-time PCR (RT-PCR), or combinations thereof.

Preferably, PCR amplification products are restricted to strands synthesized in response to RIP activity and are generated using reverse and forward oligonucleotide primers. In a preferred embodiment, reverse and forward primers (SEQ ID NOs: 3 and 4, respectively) are employed to amplify a section of the complementary strand. It is appreciated that the complements of SEQ ID NOs: 3 and 4 are similarly operable for use in the instant invention. It is further appreciated that oligonucleotide sequences that hybridize with SEQ ID NOs: 3 or 4 are also similarly operable. Finally, multiple positions are available for hybridization on the template and target strands and will be also suitable hybridization with forward and reverse primers that may or may not be used with a probe for RT-PCR.

It is appreciated the other sites on the template and target strands are similarly operable. Primer design for these and other hybridization sites are within the skill of the art. Further, the design of probes for RT-PCR analyses are similarly within the skill of the art. Numerous software programs are available to assist such as those offered by GenScript, Biosearch Technologies, and Beacon Designer from Premier Biosoft International.

Optionally, multiple amplification products are simultaneously produced in a PCR reaction that are then available for simultaneous detection and quantification. Thus, multiple detection signals are inherently produced or emitted that are separately and uniquely detected in one or more detection systems. It is appreciated that multiple detection signals are optionally produced in parallel. Preferably, a single sample is subjected to analysis for the simultaneous or sequential detection of many separate and unique substrates from one or more RIPS. Each substrate is optionally optimized for reaction with a particular RIP. Thus, multiple RIPs may be individually detected and quantified simultaneously in a single reaction. It is appreciated that three or more substrates are simultaneously or sequentially measured in the instant inventive method. Oligonucleotide matched primers are simultaneously or sequentially added and the sample is subjected to proper thermocycling reaction parameters. For detection by mass spectrometry a single sample of the amplification products from each substrate are simultaneously analyzed allowing for rapid and accurate determination of the presence of RIP activity. Optionally, analysis by RT-PCR is employed capitalizing on multiple probes with unique fluorescent signatures. Thus, each product is detected without interference by other amplification products. This multi-target approach increases confidence in quantification and provides for additional internal control.

To increase confidence and to serve as an internal or external control, a purified or otherwise characterized RIP solution is used as a sample. By amplification of a single sample with known quantities of RIP or of a set of samples representing a titration of RIP, the level of RIP activity in the unknown biological sample is determined. Preferably, the purified and characterized RIP solution is analyzed in parallel with the unknown sample to reduce inter assay error or to serve as a standard curve for quantification of unknown RIP in the sample.

The invention is operable in both a field and laboratory setting.

The invention also encompasses kits for detecting the presence of RIP activity in a sample. The kit, for example, includes a substrate capable of detecting RIP activity in a test sample and, in certain embodiments, for quantifying the RIP activity in the sample.

For oligonucleotide-based kits, the kit includes, for example: (1) an oligonucleotide substrate that is responsive to depurination by the activity of a RIP; (2) a template operable for hybridizing to a product of a RIP reaction; (3) an APE; (4) polymerase and accessory proteins; (5) a pair of primers (one forward and one reverse) useful for amplifying a nucleic acid molecule synthesized in the presence of RIP activity; and/or (6) a probe operable for detecting amplified oligonucleotide in response to RIP activity. The kit also illustratively comprises, a buffering agent, a preservative, or a protein stabilizing agent. It is appreciated that a kit is optionally as simple as a substrate for addition to a sample or as complex as all reagents, enzymes, oligonucleotides, and detection apparatus' necessary for full detection and quantification of RIP activity in a sample. The kit can also comprise components necessary for detecting the detectable agent (e.g. synthesized complementary strand). The kit can also contain a control sample or a series of control samples which is assayed and compared to the test sample contained. Each component of the kit is optionally enclosed within an individual container(s) and all of the various containers are optionally enclosed within a single package along with instructions for use.

In a preferred embodiment, the reverse and forward primers in the kit have the oligonucleotide sequence of SEQ ID NOs: 3 and 4 respectively, and a nondegenerate probe having the sequence of SEQ ID NO: 7. A kit preferably has a substrate of SEQ ID NO: 2 and a template of SEQ ID NO: 5. It is appreciated that a diagnostic kit may optionally contain primers and probes that are the complements of SEQ ID NOs: 3, 4, or 7 or that hybridize with oligonucleotides SEQ ID NOs: 3, 4, or 7. It is further appreciated that a diagnostic kit optionally includes ancillary reagents such as buffers, solvents, thermostable polymerases, nucleotides, and other reagents necessary and recognized in the art for amplification and detection of RIP in a biological sample.

Ancillary reagents are any signal producing system materials for detection of RIP activity in any suitable detection process such as RT-PCR, ELISA, mass spectrometry, western blot, immunoprecipitation, HPLC, UHPLC, or other process known in the art. In a preferred embodiment, a diagnostic kit illustratively includes a microtiter plate or other support or chamber such as a collection tube sealable or not sealable, control sample containing RIP, buffer, swab or other sample collection devices, control reagents such as competing or unlabelled reagents, control substrate and relevant primers and probes, and other materials and reagents for detection. The kit optionally includes instructions printed or in electronic form and customer support contact information. Probes in a signal producing system or otherwise are optionally labeled with a fluorophore, biotin, peroxidase, or other enzymatic or non-enzymatic detection label such as a radioactive label or otherwise.

The components of the kit are any of the reagents described above or other necessary and non-necessary reagents known in the art for solubilization, detection, washing, storage, or other need for in a diagnostic assay kit.

The current invention will quickly and conveniently determine if an unknown sample possesses enzymatic RIP activity and will greatly aid in triage of victims following suspected exposure to a RIP such as ricin. In addition, the invention will aid in initial forensic investigation by immediately determining potency at any remote location. As such, field forward personal will make estimates of purity/grade and the age of the weapon at the site of dispersal and with rapid and sensitive results. The inventive rapid screening assay to assess RIP activity will also prove beneficial to the pharmaceutical or academic research industries as a screening tool for genetically engineered RIPs developed as cancer chemotherapeutics or other therapeutics and to basic researchers identifying and characterizing new RIPs.

The present invention is further detailed with respect to the following examples. These examples are for illustrative purposes and are not intended to limit the scope of the appended claims.

Example 1

Depurination by Ricin A-Chain

100 μM of DNA oligonucleotide substrate (SEQ ID NO: 2) is reacted with 0.5 μM Ricin A chain (Sigma Chemical Co, St. Louis, Mo.) at 37° C. for 30 minutes in 10 mM potassium citrate and 1 mM EDTA (pH 4.0). Adenine release is verified with LC/MS.

Example 2

Hydrolysis of Product by APE

To perform the APE activity assay, 1 μl of the reaction product of Example 1 is hybridized to 1 μl of 100 μM template oligonucleotide (SEQ ID NO: 5) (Gene Link, Inc., Hawthorne, N.Y.) by mixing at room temperature. To this 1 unit of APE1, 1 μl of 10× NEBuffer4 (20 mM Tris-acetate, 50 mM potassium acetate, 10 mM Magnesium Acetate, 1 mM Dithiothreitol, pH 7.9 at 25° C.) (New England Biolabs) and 6 μl of molecular grade water is added. Recombinant human APE1 is purchased from New England Biolabs, Ipswich, Mass. (10,000 Units/ml) in 50% glycerol. One unit is defined as the amount of enzyme required to hydrolyze 20 μmol of a 34 by oligonucleotide duplex containing a single AP site in a reaction volume of 10 μl in one hour at 37° C. The reaction mixture is incubated for 1 hour at 37° C.

Example 3

Detection by Real-Time PCR

Following incubation, 5 μl of the reaction mix of Example 2 is added to a PCR reaction mixture (Bio-Rad, Hercules, Calif.) consisting of 12.5 μl Bio-Rad master mix, 1 μl forward primer (SEQ ID NO: 4), 1 μl reverse primer (SEQ ID NO: 3), 1 μl probe (SEQ ID NO: 7), and 4.5 μl water. Real-time PCR is performed on a Bio-Rad iCycler using Taq Polymerase (Bio-Rad). Cycle times are 95° C. for 10 minutes followed by an amplification program of 50 cycles of 3 seconds at 95° C., 5 seconds at 61° C., and 20 seconds at 72° C. with fluorescence acquisition at the end of each extension.

Figure 6:
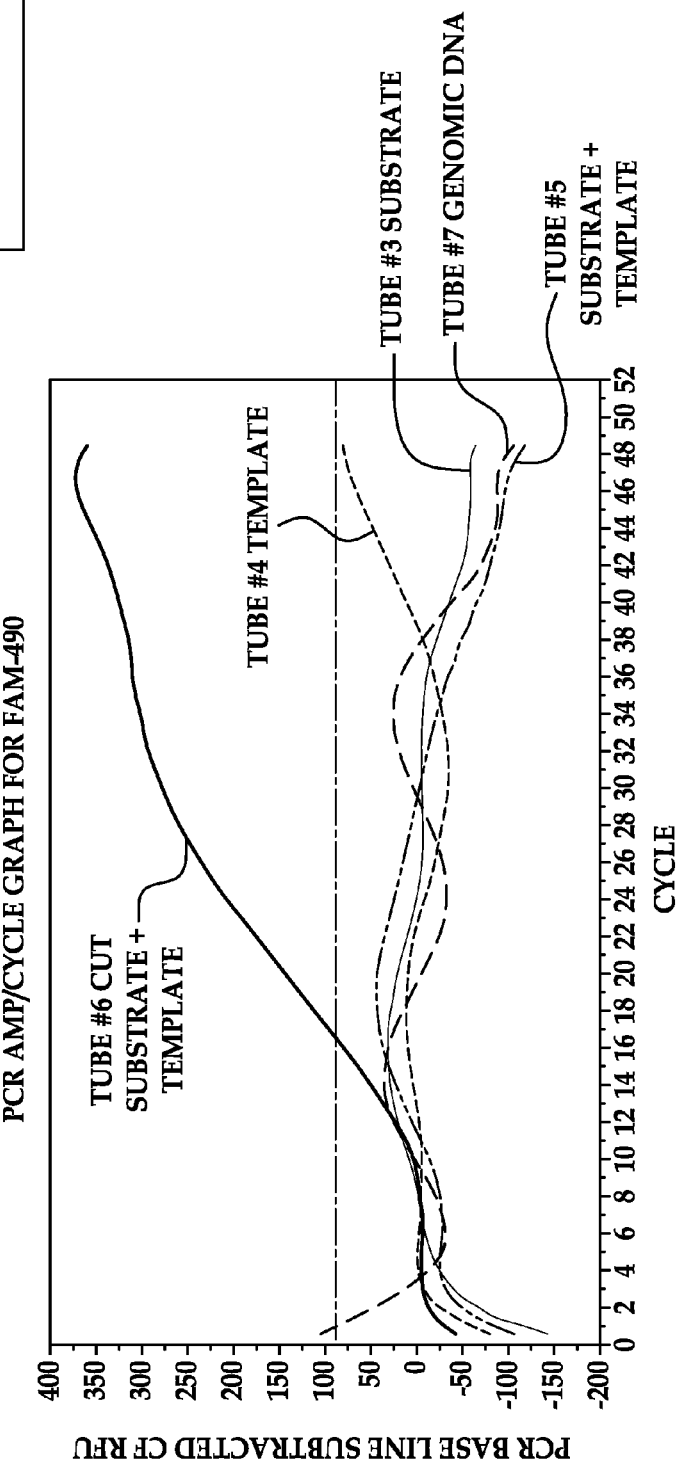
FIG. 6 is a plot of amplification of a DNA substrate with a simulated AP site as a function of PCR cycles.

The ability of a DNA substrate that was simulated to have been depurinated by a RIP and subsequently hydrolyzed by APE was examined to determine its ability to hybridize to the template DNA, followed by extension with Taq polymerase and amplification through the polymerase chain reaction. Oligonucleotide representing RIP depurinated and APE cleaved product is amplified when combined with the template, whereas full length depurinated substrate demonstrates negligible amplification. (FIG. 6).

Figure 7:
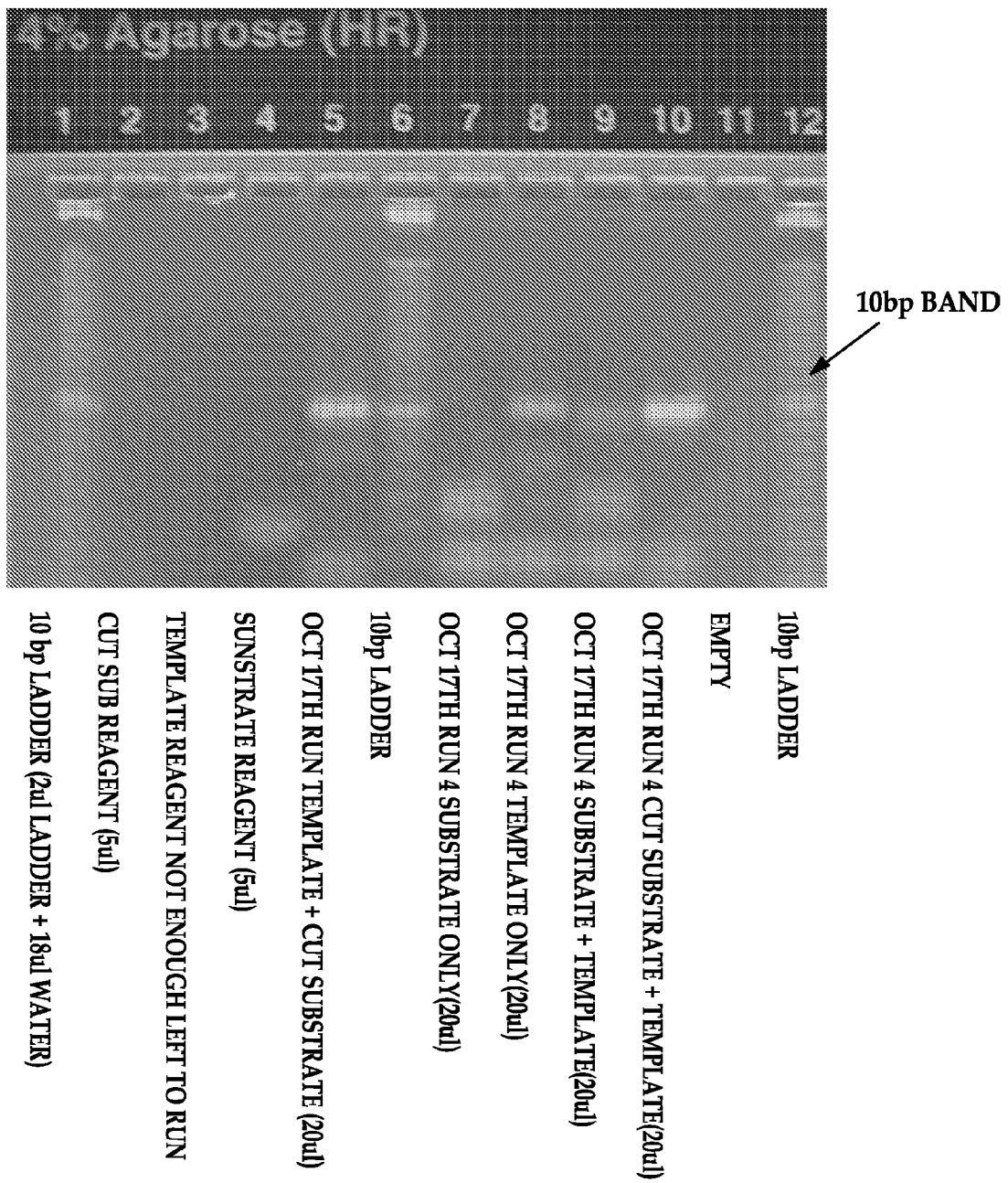
FIG. 7 is an image showing detection of amplified oligonucleotide strand complementary to the template by gel electrophoresis.

Post PCR amplification reaction products are analyzed for amplification by gel electrophoresis. In FIG. 7, lane 8 it is observed that a concentrated template solution non-specifically amplified so dilution experiments are performed to decipher a template concentration that would only demonstrate amplification in the presence of RIP and APE modified substrate. Serial dilutions are performed to determine if this non specific amplification could be resolved by using a more dilute concentration of template DNA. A 1:1,000,000 dilution template eliminates all non-specific amplification.

Figure 8:
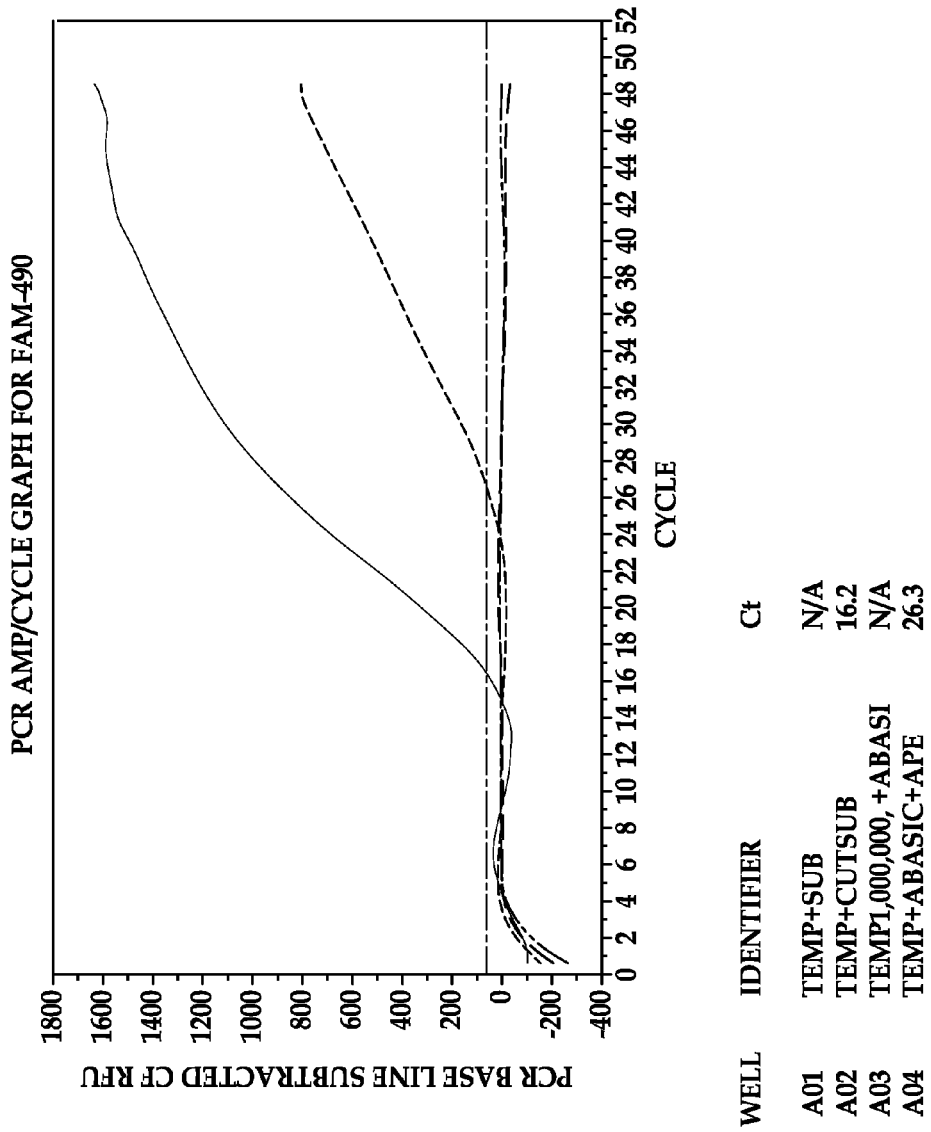
FIG. 8 is a plot of RT-PCR detection of amplified oligonucleotide strand complementary to the template following cleavage by an APE.
Figure 9:
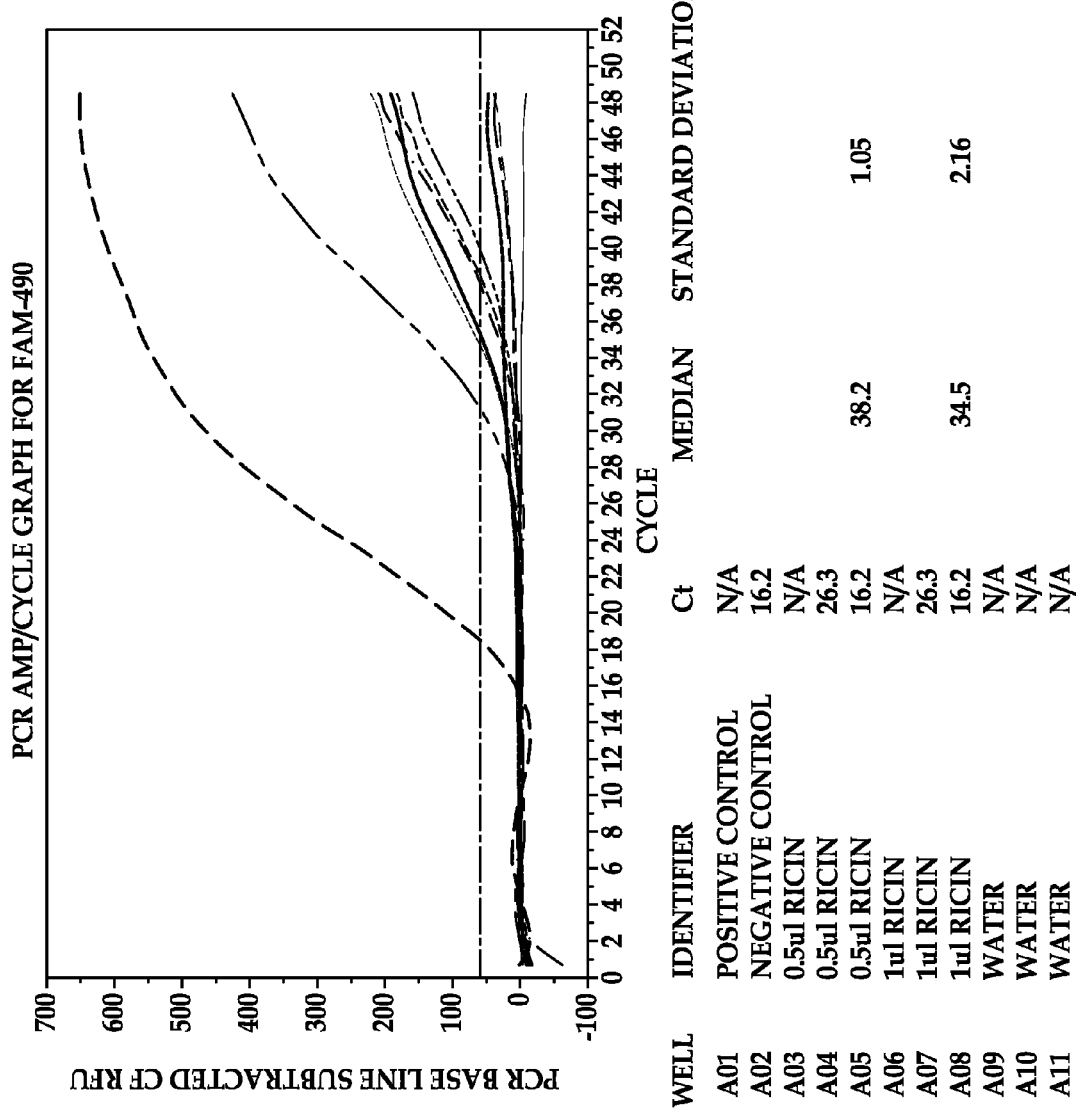
FIG. 9 is a plot of an overall detection of RIP activity by the inventive process due to action of ricin.

Substrate DNA synthesized to contain an abasic site, thus, simulating RIP depurination, is hybridized to template DNA and subjected to endonuclease activity of APE1. APE1 activity cleaves the substrate resulting in specific amplification of the template oligonucleotide. (FIG. 8)

The products of the reaction of Examples 1 and 2 are subjected to analysis by RT-PCR. Specific amplification of the oligonucleotide strand complementary to the template strand is observed with 0.5 μl or 1 μl of ricin demonstrating amplification at 38.2 cycles and 34.5 cycles respectively. Other RIPs demonstrate similar amplification results in the inventive method as illustrated by Table I.

TABLE I

| RIP | Count |
|---|---|
| Abrin | 36.2 |
| RCA120 | 38.5 |
| Viscumin | 26.2 |
| Volkensin | 42.1 |
| Shiga toxin | 35.6 |
| Gelonin | 25.7 |
| PAP | 24.3 |
| Saporin-L1 | 26.2 |
| Trichokirin | 35.5 |

REFERENCE LIST

1. U.S. Pat. No. 6,864,056
2. U.S. Pat. No. 7,033,764
3. Amukele T K and Schramm V L, *Biochemistry,* 2004; 43(17):4913-22
4. Barbieri, L, et al, *Biochem. J,* 1996; 319, 507-13
5. Endo, Y, et al, *J Biol Chem,* 1987; 262:8128-30
6. Endo, Y, *J Biol Chem,* 1988; 263:8735-8739
7. Johnson, *Annual Reviews of Biochemistry,* 1993: 62:685-713
8. Kradic, K W, et al., *Clin Chem,* 2004; 50: 1080-1082
9. Kunkel, *Journal of Biological Chemistry,* 1992; 267: 18251-18254
10. Lennerstrand, *Analytical Biochemistry,* 1996; 235:141-152
11. Ljungquist, L, et al., *J Bacteriol,* 1976; 126:646-653
12. Ma, W, et al, *Nucleic Acids Res,* 2008; 36:1836-1846
13. Peumans, W J et al., *FASEB J,* 2001; 15:1493-1506
14. Suzuki, T, et al, *Nucleic Acids Res,* 1994; 22:4997-5003
15. Yin et al., *Science,* 1995; 270: 1653-57
16. Zaky, A, et al., *Nucleic Acids Res,* 2008; 36: 1555-1566

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

What is claimed is:

1. A process for detecting activity of a ribosome inactivating protein, comprising:

providing an oligonucleotide substrate consisting of SEQ ID NO: 2 with a GAGA loop;

contacting said substrate with a sample containing a ribosome inactivating protein to produce a product;

hybridizing said product to a template;

cleaving said product with an endonuclease;

extending said product by a polymerization reaction to form an oligonucleotide strand complementary to said template; and detecting said oligonucleotide strand complementary to said template.

2. The process of claim 1, wherein said endonuclease is apurinic/apyrimidinic endonuclease.

3. The process of claim 1, wherein said substrate does not form a thermodynamically stable stem-loop.

4. The process of claim 1, wherein said template is selected from the group consisting of SEQ ID NO: 5 and SEQ ID NO: 6.

5. The process of claim 1, wherein said detecting is by a method selected from the group consisting of RT-PCR, mass spectrometry, and HPLC.

6. The process of claim 1, wherein said extending said product by a polymerisation reaction uses primers selected from the group consisting of SEQ ID NO: 3, SEQ ID NO: 4, and SEQ ID NO: 8.

7. A process for detecting ribosome inactivating protein in a sample, comprising:

providing an oligonucleotide substrate of SEQ ID NO: 1;

contacting said substrate with a sample containing a ribosome inactivating protein to produce a product;

hybridizing said product to a template of SEQ ID NO: 6;

cleaving said product with an endonuclease;

extending said product by a polymerization reaction to form an oligonucleotide strand complementary to said template; and detecting said oligonucleotide strand complementary to said template by RT-PCR.

8. The process of claim 7, wherein said endonuclease comprises an apurinic/apyrimidinic endonuclease.

9. The process of claim 7, wherein detecting said oligonucleotide strand is by using a probe of SEQ ID NO: 7; wherein hybridizing said probe is under conditions suitable for a polymerase chain reaction; and detecting a first detection signal from said probe hybridized to said oligonucleotide strand complementary to said template.

10. The process of claim 9, further comprising comparing said first detection signal to a second detection signal, wherein said second detection signal results from the hybridization of a probe complementary to a second template sequence.

11. The process of claim 10, wherein said second detection signal is generated in parallel with said first detection signal.

12. The process of claim 11, wherein said first detection signal is compared to a third detection signal from a ribosome inactivating protein calibrator extracted in parallel to said sample.

13. The process of claim 12, wherein said ribosome inactivating protein calibrator comprises a known amount of ribosome inactivating protein and a known amount of a medium similar to the sample.

14. The process of claim 13, further comprising confirming said detection signal with a protein based ribosome inactivating protein detection assay.

15. The process of claim 7, wherein said detecting diagnoses ribosome inactivating protein intoxication in a human.

16. The process of claim 7, wherein said oligonucleotide strand complementary to said template is generated by PCR extension from a product generated by a purified and titered ribosome inactivating protein solution.

* * * * *